US 10,682,622 B1

(12) United States Patent
Gaillard et al.

(10) Patent No.: US 10,682,622 B1
(45) Date of Patent: Jun. 16, 2020

(54) MICRO-FLUID REACTOR WITH IN-PLANE MICRO-LENSES

(71) Applicants: William Randall Gaillard, Madison, AL (US); John D. Williams, Decatur, AL (US)

(72) Inventors: William Randall Gaillard, Madison, AL (US); John D. Williams, Decatur, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 191 days.

(21) Appl. No.: 15/585,745

(22) Filed: May 3, 2017

(51) Int. Cl.
*B01J 19/00* (2006.01)
*G02B 6/32* (2006.01)
*G02B 3/06* (2006.01)
*C12M 1/40* (2006.01)

(52) U.S. Cl.
CPC .......... *B01J 19/0093* (2013.01); *C12M 21/18* (2013.01); *G02B 3/06* (2013.01); *G02B 6/32* (2013.01); *B01J 2219/0097* (2013.01); *B01J 2219/00801* (2013.01)

(58) Field of Classification Search
CPC .................................................... B01J 19/0093
USPC ........................................................ 422/502
See application file for complete search history.

(56) References Cited

PUBLICATIONS

Cheng et al. "Freestanding optical fibers fabricated in a glass chip using femtosecond laser micromachining for lab-on-a-chip application" Opt Express. Sep. 5, 2005;13(18):7225-32. (Year: 2005).*
Cheng and Tsai et al. "Fabrication of 3D microoptical lenses in photosensitive glass using femtosecond laser micromachining" Appl. Phys. A 85, 11-14 (2006) (Year: 2006).*
Pires, et al., "Recent Development in Optical Detection Technologies in Lab-on-a-Chip Devices for Biosensing Applications," Sensors, 2014, p. 15458-15479, vol. 14.
Gu, et al., "Microfluidic sensing: state of the art fabrication and detection techniques," Journal of Biomedical Optics, Aug. 2011, p. 1-13, vol. 16.
Lee, et al., "Optical Imaging Techniques in Microfluidics and their Applications," Lab Chip, 2012, p. 3566-3575, vol. 12.
He, at al., "Femtosecond Laser Fabrication of Monolithically Integrated Microfluidic Sensors in Glass," Sensors, 2014, p. 19402-19440, vol. 14.
Fan, et al., "Optiofluidic Microsystems for Chemical and Biological Analysis," Nat Photonics, 2011, p. 591-597.

(Continued)

*Primary Examiner* — Christine T Mui
*Assistant Examiner* — Emily R. Berkeley
(74) *Attorney, Agent, or Firm* — Maynard Cooper & Gale, P.C.; Jon E. Holland (57) ABSTRACT

A micro-fluidic reactor may comprise a photosensitive glass substrate with a plurality of features produced by etching. The features may include micro-channels, micro-lenses, and slots for receiving optical fibers. During operation of the micro-fluidic reactor, the optical fibers may transmit optical signals for measuring characteristics of fluid reagents and reactions taking place. The micro-lenses may focus optical signals from the optical fibers to create an approximately collimated optical path for the optical signals, reducing optical spread and enhancing fiber-to-fiber optical power coupling.

5 Claims, 6 Drawing Sheets

(56) References Cited

PUBLICATIONS

Bragheri, et al., "Optofluidics for Biophotonic Applications," IEEE Photonics Journal, 2012, p. 596-600, vol. 4, (2).

Schafer, et al., Microfluidic Cell Counter with Embedded Optical Fibers fabricated by Femtosecond Laser Ablation and Anodic Bonding, Optics Express, 2009, p. 6068-6073, vol. 17 (8).

Queste, et al., "Manufacture of Microfluidic Glass Chips by Deep Plasma Etching, Femtosecond Laser Ablation, and Anodic Bonding," Microsystems Technology, 2010, p. 1485-1493, vol. 32 (11).

Tantawi, et al., "In-Plane Spectroscopy of Microfluidic Systems made in Photosensitive Glass," Microsystems Technology, 2012, p. 173-177, vol. 19 (2).

Camou, et al., "PDMS 2D Optical Lens Integratedwith Microfluidic Channels: Principle and Characterization," Lab Chip, 2003, p. 40-45, vol. 3 (1).

\* cited by examiner

MICRO-FLUID REACTOR WITH IN-PLANE MICRO-LENSES

STATEMENT REGARDING FEDERALLY SPONSORED RESEARCH OR DEVELOPMENT

This invention was made with Government support under contract ALEPSCoR GSRP EPS-1158862 awarded by the National Science Foundation. The Government has certain rights in the invention.

RELATED ART

Micro-fluidic reactors enhance performance and provide new functionalities that are not possible at larger scales. However, suitable materials must be used in order to perform and observe experiments using micro-fluidic reactors. A micro-fluidic reactor may introduce one or more micro-fluids into a reaction chamber where reactions may be observed.

Observations of chemical reactants may be achieved using optical signals. While properties of glass make it well suited for use in enzyme reactors, chromatography, and chemical synthesis, glass also has an optical transparency window suitable for many applications. However, using conventional methods for fabricating embedded glass microstructures generally results in glass with translucent or opaque surfaces. Such structures are not suitable for optical applications because abnormalities of the surfaces of the glass cause light to defocus, diminishing quality of optical signals and decreasing optical power. Thus, improved glass microstructures for facilitating optical applications are generally desirable.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure generally pertains to a glass micro-fluidic reactor with in-plane micro-lenses. A micro-fluidic reactor may include a glass substrate having a plurality of micro-channels and a reaction chamber formed by etching. A micro-channel or reaction chamber may include one or more reagent ports coupled to a plurality of reservoirs for storing one or more reagent fluids. The micro-channels may introduce the one or more reagent fluids into the reaction chamber for producing a desired reaction. A voltage may be applied to the reactor to induce electroosmotic flow (EOF) to pump or propel a reagent fluid along a micro-channel (e.g., toward the reaction chamber). The voltage may be applied at an inlet port and a corresponding outlet port of a micro-channel for providing controlling reagent fluid flow as desired. To further improve control, the reaction chamber may be packed with microbeads. The microbeads may improve flow velocity control by forming nanocapillaries through which a reagent fluid may flow, and increasing surface area for reactions within the micro-fluidic reactor.

Optical fibers may be used for monitoring or measuring characteristics of reagent fluids, conditions within the micro-fluidic reactor, reaction progress, or other information. The micro-fluidic reactor may comprise a plurality of slots orthogonal to the plurality of micro-channels for receiving the optical fibers. A source optical fiber may be inserted into a first slot on a first side of micro-channel, and a detection fiber may be inserted into a corresponding second slot on a second side of the micro-channel to receive optical signals from the source fiber. One or more micro-lenses may be positioned between the source fiber and a first wall of the micro-channel for directing an optical signal from the source fiber across a width of the micro-channel toward one or more micro-lenses positioned between the detection fiber and a second wall of the micro-channel.

Figure 1:
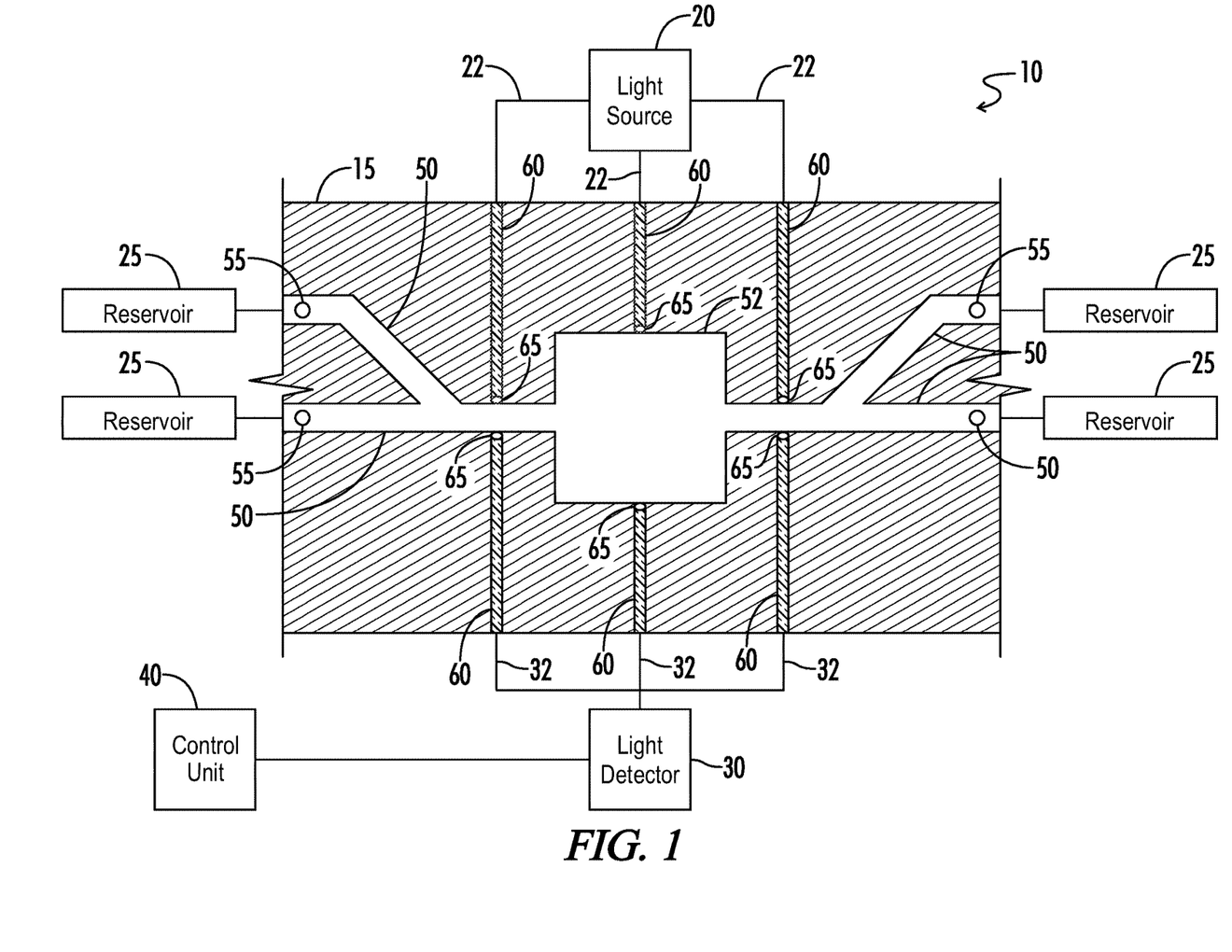
FIG. 1 depicts a micro-fluidic reactor in accordance with some embodiments of the present disclosure.

FIG. 1 depicts an exemplary embodiment of a micro-fluidic reactor 10 in accordance with some embodiments of the present disclosure. The micro-fluidic reactor 10 may comprise a reusable glass substrate 15, and may be coupled to a light source 20 via at least one optical fiber 22. The substrate 15 may be coupled to at least one reservoir 25 for storing one or more reagent fluids. The substrate 15 also may be coupled to a light detector 30 via one or more optical fibers 32 for receiving optical signals, as will be described in further detail below. In some embodiments, the micro-fluidic reactor 10 may be coupled to a control unit 40 for generally controlling the functionality of the micro-fluidic reactor 10, such as by providing signals to and receiving signals from various resources, such as the light source 20, or light detector 30. Control unit 40 also may control other operations of the micro-fluidic reactor 10, such as managing a voltage applied across substrate 15 for facilitating EOF. In other embodiments, the micro-fluidic reactor 10 may comprise other additional components and be arranged in other configurations for achieving the functionality described herein.

In an exemplary embodiment, substrate 15 may include one or more micro-channels 50 for channeling reagent fluids through substrate 15 to the reaction chamber 52. Each of the micro-channels 50 may have desired characteristics (e.g., dimensions, shape or otherwise) for permitting flow of reagent fluids from their respective reservoirs 25 through the substrate 15 via EOF. Other techniques for propelling reagent fluids through micro-fluidic reactor 10 may be used in other embodiments. In some embodiments, substrate 15 may be a packed bed micro-fluidic reactor, and reaction chamber 52 or, in some embodiments, each micro-channel 50 may be packed with a plurality of microbeads. In addition, the substrate 15 of FIG. 1 is shown as comprising a single layer, but the substrate 15 may have other numbers of layers in other embodiments.

In an embodiment, micro-fluidic reactor 10 may propel one or more reagent fluids via EOF using a voltage differential from a power source (not specifically shown in FIG. 1) applied across the micro-fluidic reactor 10. In an embodiment, each of the one or more reagent fluids present within one or more reservoirs 25 may have a net charge near channel walls that allows them to move within an electrical field. In an embodiment, a voltage may be applied across the micro-fluidic reactor 10 (e.g., substrate 15) to propel the one or more reagent fluids from the one or more respective reservoirs 25 through one or more respective reagent ports 55 (e.g., an inlet port 55) and into one or more micro-channels 50. A voltage also may be applied to an opposite side of the micro-fluidic reactor 10 (e.g., an outlet port 55). The voltage differential may cause the one or more reagent fluids to flow from a reagent port 55 (e.g., an inlet port 55) to the reaction chamber 52 via a micro-channel 50. Likewise, the voltage differential may cause the reagent fluid to flow out of the reaction chamber 52 to another reagent port 55 (e.g., an outlet port 55) via a micro-channel 50. Other techniques for propelling reagent fluids through substrate 15 may be possible in other embodiments.

In an exemplary embodiment, light source 20, light detector 30, optical fibers 22 and optical fibers 32 may form a fiber-optic system for performing in-plane optical fiber spectroscopy, such as for monitoring characteristics of reagent fluids and reaction products within the micro-fluidic reactor 10. Additional details of fiber-to-fiber coupling in micro-fluidic reactor 10 will be described below. In some embodiments, characteristics such as color, density, and concentration (e.g., synthesized oligonucleotide concentration or otherwise) of a reactant fluid may be measured, monitored, or otherwise, based on analysis of the light signal transmitted through the substrate 15. In some embodiments, the light source 20 may generate a light signal for transmission over one or more optical fibers 22, emission through reaction chamber 52 or a micro-channel 50 within the substrate 15, receipt by one or more optical fibers 32, and detection by a light detector 30.

Although a micro-fluidic reactor 10 in accordance with some embodiments of the present disclosure may be fabricated according to a variety of techniques, exemplary fabrication techniques and methods for producing a micro-fluidic reactor in accordance with some embodiments of the present disclosure will be described. It will be understood that techniques for fabrication described herein are not intended to limit the possible methods for fabrication of the a micro-fluidic reactor in accordance with some embodiments of the present disclosure, and that substitution of one or more techniques while achieving the functionality described herein is within capabilities of one of ordinary skill in the art.

In some embodiments, substrate 15 may be a glass substrate having a suitable aspect ratio (e.g., approximately 50:1 or otherwise) for achieving the functionality set forth herein. As described herein, it may be desirable for substrate 15 to have characteristics and properties of glass (e.g., high transparency, low auto-fluorescence, chemical resistance, thermal and electrical properties, and compatibility with silanol-based chemistries). In an embodiment, the substrate 15 may be a photosensitive glass, such as borosilicate APEX™ photosensitive glass, though other materials may be possible in other embodiments. In an exemplary embodiment, the substrate 15 may undergo various processing, such as receiving a dose of ultraviolet (UV) light (e.g., an approximate 7 Joule dose or other amount). Other treatments or processing may be performed in other embodiments in response to various variables, including substitution of the type of glass used for substrate 15.

In an embodiment, glass substrate 15 may undergo processing and etching to produce desired features and properties. In some embodiments, the substrate 15 may be cleaned prior to etching, such as by rubbing with ethanol and rinsing with ethanol and acetone and exposure to a nitrogen stream for drying. Other cleaning techniques may be used in other embodiments for preparing the substrate 15 for etching.

In some embodiments, each of the plurality of micro-channels 50, micro-lenses 65, slots (described further below), and other features of substrate 15 may be produced by etching of the glass substrate 15. As an example, in some embodiments, a masking material (e.g., a quartz photomask) having a desired pattern may be applied to portions of a surface of the substrate 15 corresponding to a desired location of the plurality of micro-channels 50, micro-lenses 65, or other characteristics of the micro-fluidic reactor 10. Note that a photomask may be patterned to produce various features of substrate 15. Photomask patterns for etching micro-lenses 65 and slots for receiving optical fibers 60 will be described in further detail below.

In some embodiments, the substrate 15 may be placed between (e.g., sandwiched) two adjacent substrates and exposed to a photothermal cycle (e.g., baked by exposure to high temperature, such as over 550° C.). In some embodiments, the adjacent substrates may be alumina, but other materials are possible in other embodiments. In an exemplary embodiment, the baking may be performed in a programmable furnace and may comprise increasing temperature (e.g., ramping at approximately 6° C./min) of the substrate 15 from room temperature to approximately 500° C. for approximately 75 minutes, then increasing the temperature (e.g., ramping at approximately 2° C./min) to approximately 555° C. After a dwell period (e.g., approximately 80 minutes or other time), the temperature of the substrate 15 may be decreased (e.g., ramped down at approximately 2° C./min) to room temperature.

In some embodiments, patterned glass on the substrate 15 may be preferentially etched when exposed to a suitable acid, such as approximately 10% hydrofluoric acid (HF), for an appropriate amount of time (e.g., approximately 1 hour exposure). Desired etching may be performed based on an amount of time corresponding to a concentration of acid to which the substrate 15 is exposed and a duration of the exposure, although other etching techniques may be utilized in other embodiments. Patterned portions of the glass may be completely removed as a result of the etching process, and thickness of the substrate may be decreased (e.g., from approximately 500 µm to approximately 400 µm or other thickness) as a result of the etching.

In some embodiments, substrate 15 may undergo additional treatment during fabrication, such as annealing to seal the micro-fluidic reactor 10 and to reduce surface roughness caused by the etching process (e.g., roughness of surfaces in micro-channels created by etching) or otherwise. In some embodiments, the annealing of substrate 15 may further provide the benefit of removing surface contaminants from the substrate 15. However, such processing may remove silanol sites, which removal may be undesirable, as described further below. In some embodiments, silanols may be restored or recovered by exposing the substrate 15 to compounds such as sodium hydroxide (NaOH) in appropriate concentrations and for appropriate durations (e.g., by dipping the substrate 15 in approximately 1M NaOH for approximately 10 minutes). Other methods for restoring silanols may be implemented in other embodiments.

Figure 2:
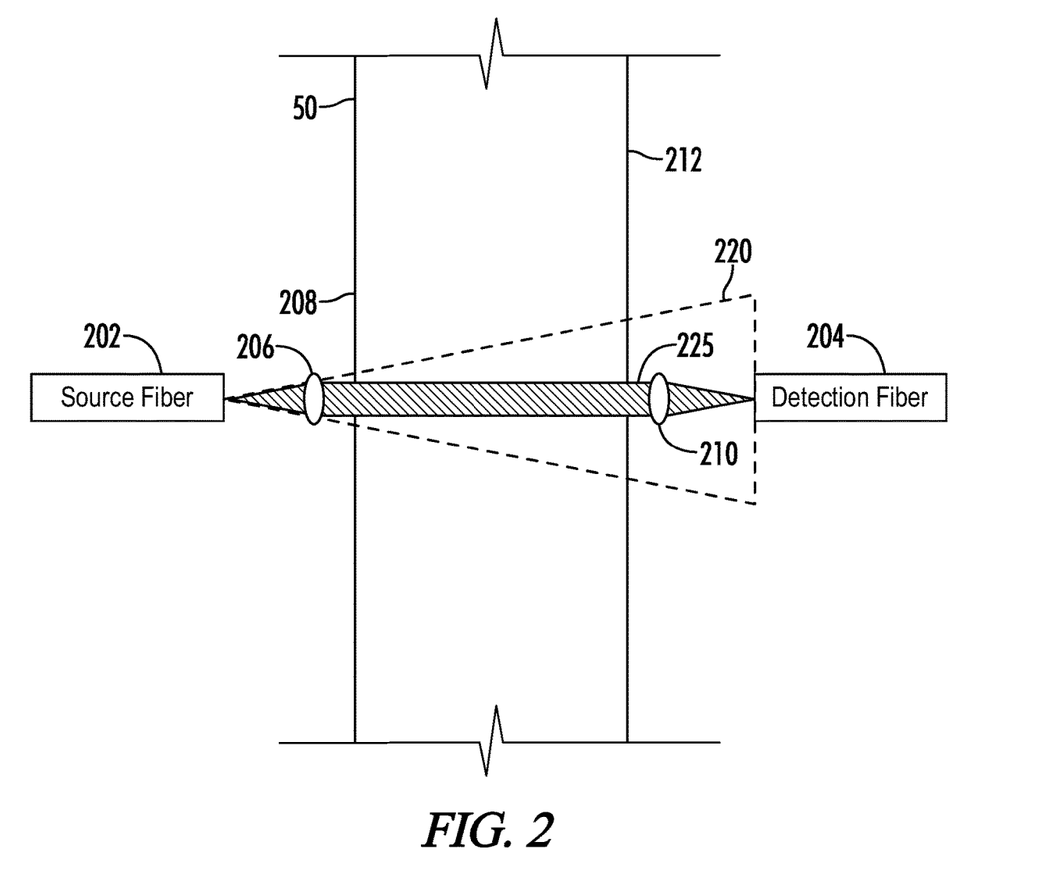
FIG. 2 depicts a diagram of a top view of a micro-channel with micro-lenses for directing optical fiber signals in accordance with some embodiments of the present disclosure.

FIG. 2 depicts a diagram of a top view of a micro-channel 50 with micro-lenses for directing optical fiber signals. Although micro-lenses may be fabricated at various areas of the substrate 15 (e.g., walls of the reaction chamber 52 or otherwise), the present discussion of FIG. 2 describes micro-lenses positioned along walls of one of the micro-channels 50. The embodiment of FIG. 2 comprises a micro-channel 50, source fiber 202, a detection fiber 204, a first micro-lens 206, and a second micro-lens 210. In an exemplary embodiment, source fiber 202 and detection fiber 204 may be aligned such that a signal of light from a source fiber 202 may be received by detection fiber 204. The first micro-lens 206 and second micro-lens 210 may refract light transmitted by source fiber 202 and received by detection fiber 204 so that optical power of the transmitted light is preserved (e.g., optical coupling between source fiber 202 and detection fiber 204) and loss of light due to light spread and alignment errors is reduced. Although the embodiment of FIG. 2 depicts particular components in a particular arrangement, it will be understood that one of ordinary skill in the art will appreciate other possible variations, and, in other embodiments, any number of source fibers 202, detection fibers 204, and micro-lenses 206 and 210 are possible.

In some embodiments, source fiber 202 may be positioned to transmit an optical signal across micro-channel 50 for detection by a detection fiber 204. The source fiber 202 may be positioned so that its longitudinal axis is approximately orthogonal to a transverse axis of a first micro-channel wall 208 of micro-channel 50. Similarly, detection fiber 204 may be positioned to receive an optical signal from source fiber 202, and may be positioned so that its longitudinal axis is approximately orthogonal to a transverse axis of a second micro-channel wall 212 of micro-channel 50. In some embodiments, first micro-channel wall 208 and second micro-channel wall 212 may be substantially flat and have a desired transparency for allowing light to pass through. First micro-lens 206 and second micro-lens 210 may be positioned at various distances from first micro-channel wall 208 and second micro-channel wall 212, respectively for achieving desired interaction with (e.g., refracting, focusing, etc.) light. In other embodiments, other orientations of source fiber 202, detection fiber 212 and micro-channel walls 208 and 212 are possible.

In an exemplary embodiment, a first micro-lens 206 may be positioned between the source fiber 202 and the first micro-channel wall 208 for refracting light of optical signals from source fiber 202. In some embodiments, the micro-lens 206 may be spherical, toric, cylindrical, or otherwise shaped or dimensioned to refract the light emitted from the source number 202 in a desired manner before it reaches micro-channel wall 208 and is transmitted across the micro-channel 50. Other configurations and orientations of source fiber 202 and micro-lens 206 are possible in other embodiments. In some embodiments, micro-lens 206 may comprise a plurality of micro-lenses, although a single micro-lens 206 is depicted in FIG. 2 for simplicity.

In an exemplary embodiment, a second micro-lens 210 may be positioned between detection fiber 204 and a second micro-channel wall 212. An optical signal may cross micro-channel 50 and second micro-channel wall 212, and the second micro-lens 210 may further refract the optical signal to narrow or focus the transmitted light. In this regard, refraction of the optical signal by the second micro-lens 210 may improve reception of the optical signal by detection fiber 204. In some embodiments, micro-lens 210 may have any shape for refracting light in a desired manner for reception by detection fiber 204 (e.g., spherical, toric, cylindrical, or otherwise). In some embodiments, micro-lens 210 may comprise a plurality of micro-lenses, although a single micro-lens 210 is depicted in FIG. 2 for simplicity.

Examples of operation of micro-lenses 206 and 210 in the embodiment of FIG. 2 will now be described in further detail. FIG. 2 depicts dashed lines indicative of a predicted path 220 typical of an unfocused optical signal from source fiber 202 (e.g., in absence of both of micro-lenses 206 and 210). The path 220 of FIG. 2 demonstrates a spread or scattering of light emitted from a single source (e.g., a point), such as source fiber 202. As shown by FIG. 2, un-refracted signals of light from source fiber 202 may result in a broadening propagation path (e.g., path 220) in absence of corrective refraction by a micro-lens (e.g., micro lens 206). In this regard, optical signals following path 220 may result in decreased optical power received by detection fiber 204.

Addition of micro-lenses 206 and 210 may enhance optical power coupling between source fiber 202 and detection fiber 204. In an exemplary embodiment, micro-lens 206 may be positioned at an appropriate distance from source fiber 202 and may be configured to refract optical signal from source fiber 202. In this regard, micro-lens 206 may refract the optical signal to produce approximately collimated light that may follow a focused path 225 across micro-channel 50. In some embodiments, the approximately collimated light following focused path 225 may comprise substantially parallel light waves. In an exemplary embodiment, micro-channel walls 208 and 212 may be sufficiently transparent so that further refraction of incident light (e.g., following focused path 225) sufficient to cause unwanted spread of the light does not occur. After light on focused path 225 passes micro-channel wall 212, micro-lens 210 may refract the light to further focus or narrow a path of the light for detection by detection fiber 204 (e.g., by a single point). In this regard, micro-lenses 206 and 210 may enhance fiber-to-fiber optical coupling and improve optical power signal efficiency for light transmitted across micro-channel 50.

Note that, in some embodiments, micro-lenses 206 and 210 may be configured to focus light such that a focal point is created within the micro-channel 50 (not depicted in FIG. 2). In this regard, the micro-lenses 206 and 210 may focus light such that focused path 225 may have a focal point at a desired location within micro-channel 50, as opposed to comprising substantially parallel (e.g., approximately collimated) light waves. In some embodiments, light following focused path 225 may follow various paths and be focused (e.g., refracted, etc.) by the micro-lenses 206 and 210 for achieving a desired functionality based on a user's application.

Figure 3:
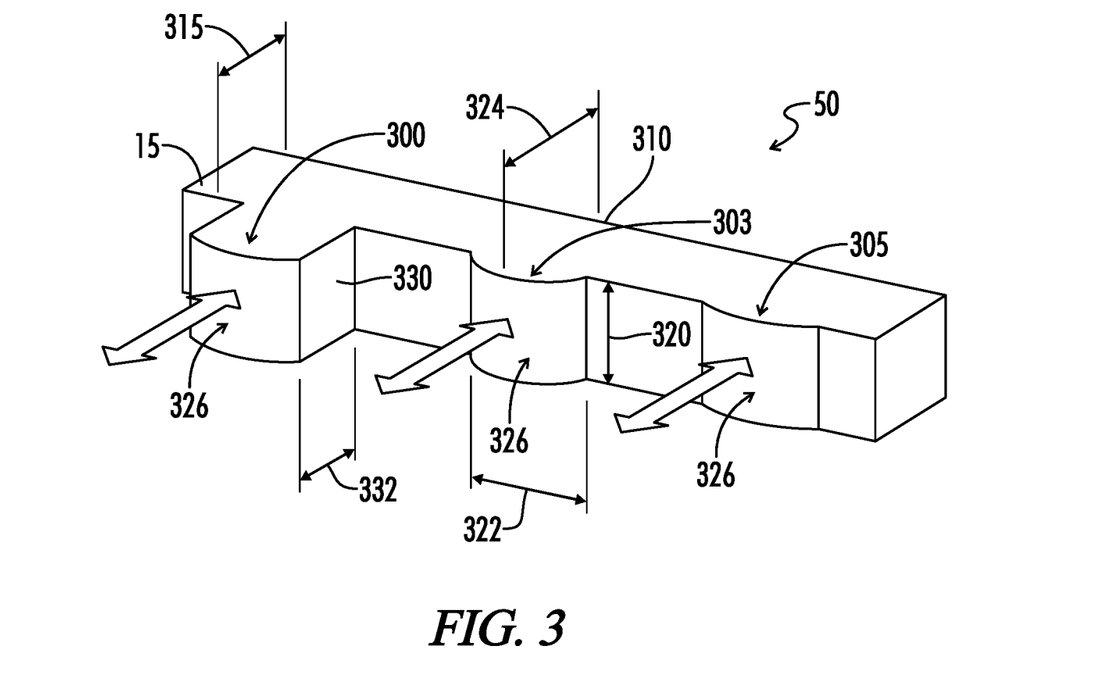
FIG. 3 depicts a three-dimensional perspective view of a cross-section of a micro-fluidic reactor substrate with a plurality of cylindrical micro-lenses in accordance with some embodiments of the present disclosure.

FIG. 3 depicts a three-dimensional perspective view of a of a micro-fluidic reactor substrate 15 with a plurality of cylindrical micro-lenses 300, 303 and 305. In some embodiments, the plurality of micro lenses 300, 303 and 305 may be positioned to refract optical signals from a plurality of source fibers (not specifically shown in FIG. 3.) before detection by a plurality of detection fibers (not specifically shown in FIG. 3.), such as is described above with regard to FIG. 2. The embodiment of FIG. 3 depicts the plurality of micro-lenses 300, 303 and 305 fabricated as features of substrate 15, although in other embodiments, a micro-lens 300, 303 or 305 may be fabricated as a freestanding micro-lens, and may be oriented in any desired position for enhancing fiber-to-fiber optical coupling (e.g., an efficiency of fiber-to-fiber optical coupling for preserving optical power).

In some embodiments, micro-lenses 300, 303 and 305 may be oriented adjacent to one another and opposite an approximately vertical micro-channel wall 310 of micro-channel 50. In some embodiments, each of micro-lenses 300, 303 and 305 may have a base thickness 315, a height 320, width 322, and lens thickness 324. Varying dimensions of micro-lenses 300, 303 and 305 may vary optical characteristics of micro-lenses 300, 303 and 305, such that the micro-lenses 300, 303 and 305 may be configured to achieve desired enhancement of fiber-to-fiber coupling of optical signals. Each micro-lens 300, 303 and 305 may have a shape, size, transparency, refractive index, or other characteristics based on desired optical characteristics of each micro-lens 300, 303 and 305 (e.g., transparency, focal length, etc.). Note that, in some embodiments, a desired refraction of light may be different for each of 300, 303 and 305.

In addition, each micro-lens 300, 303 and 305 may comprise a respective lens surface 326, having a desired shape (e.g., radius of curvature). In the embodiment of FIG. 3, each of the respective lens surfaces 326 of micro-lenses 300, 303 and 305 comprises an approximately convex shape, although other shapes of each respective lens surface 326 are possible in other embodiments. Note that a radius curvature of each of the respective lens surfaces 326 may remain constant or may vary along a lens height 320 of each respective micro-lens 300, 303 and 305. In some embodiments, variations in a radius of curvature along a lens height 320 of any of micro-lenses 300, 303 or 305 may result as part of the fabrication process for the features of substrate 15 (including micro-lenses 300, 303 and 305) as discussed below. It has been observed that such deformations, variations or distortions of desired micro-lens dimensions caused by surface tension may be reduced or eliminated in micro-lenses including a pedestal. In the embodiment of FIG. 3, micro-lens 300 comprises a pedestal 330 having a pedestal thickness 332. In some embodiments, a pedestal 330 may be positioned between substrate 15 and micro-lens face 326 in order to achieve a desired thickness (e.g., a focal length or other lens characteristic) of a micro-lens 300, 303, or 305. Varying a thickness of a micro-lens thickness 300, 303, or 305 may increase or decrease a focal length or other optical properties of a micro-lens 300, 303, or 305. Other configurations of micro-lenses 300, 303 and 305 are possible in other embodiments.

Figure 4:
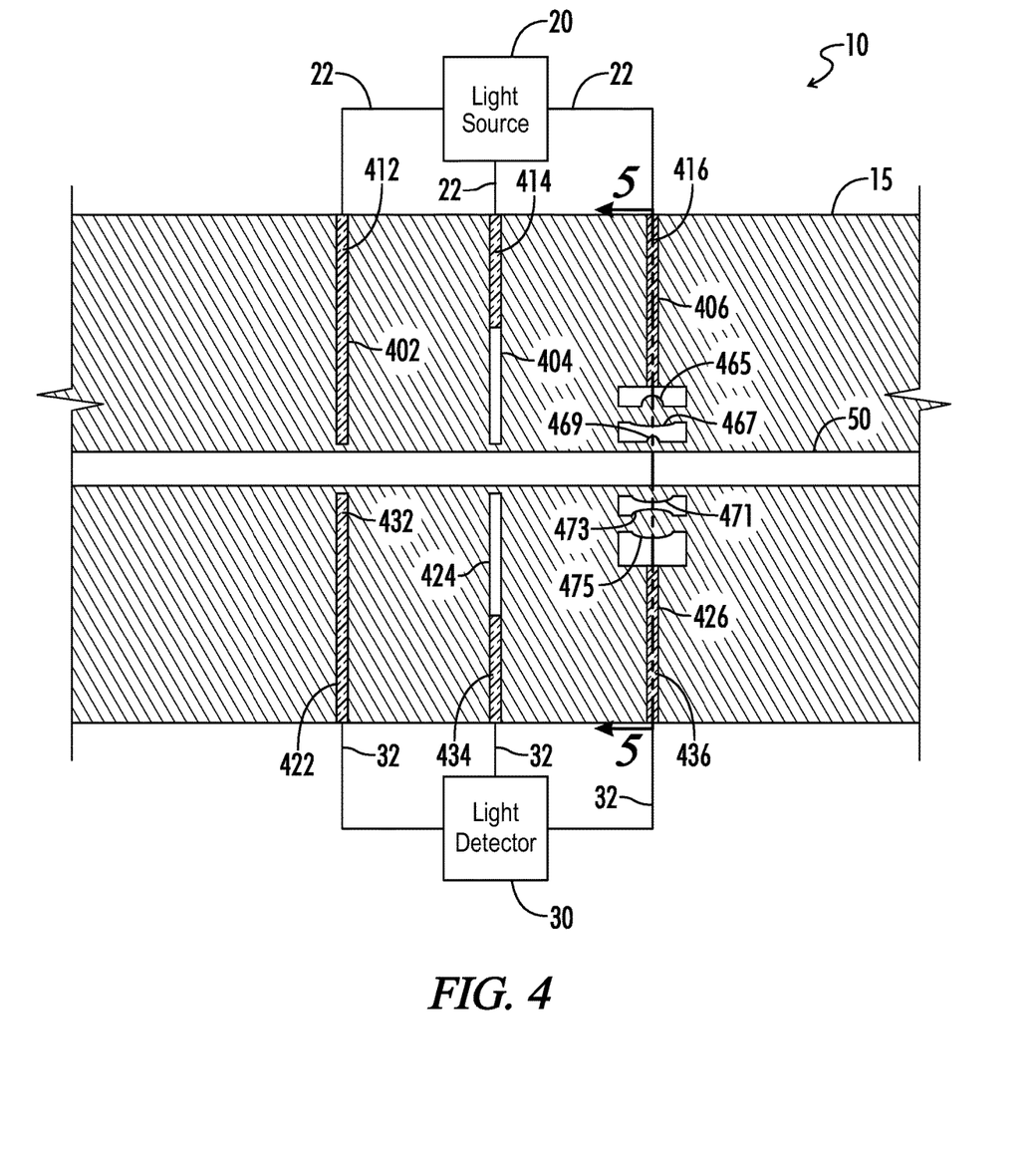
FIG. 4 depicts a top view of a micro-fluidic reactor with in-plane micro-lenses in accordance with some embodiments of the present disclosure.

FIG. 4 depicts a top view of a micro-fluidic reactor 10 with a plurality of in-plane micro-lenses. The embodiment of FIG. 4 is substantially similar to the embodiment of FIG. 1, except that the microfluidic reactor 10 of FIG. 4 includes a light source 20, a plurality of optical fibers 22 a plurality of optical fibers 32 and a light detector 30. In addition, the substrate 15 comprises a micro-channel 50 etched into substrate 15, together with a first plurality of slots 402, 404 and 406 for receiving a plurality of source optical fibers 412, 414, and 416. Substrate 15 further comprises a second plurality of slots 422, 424, and 426 for receiving a plurality of detection fibers 432, 434, and 436. The substrate 15 depicted by FIG. 4 comprises a first plurality of micro-lenses 465, 467 and 469 positioned between slot 406 and micro-channel 50 and a second plurality of micro-lenses positioned between slot 426 and micro-channel 50. Substrate 15 may comprise other components or features in other embodiments.

Figure 5:
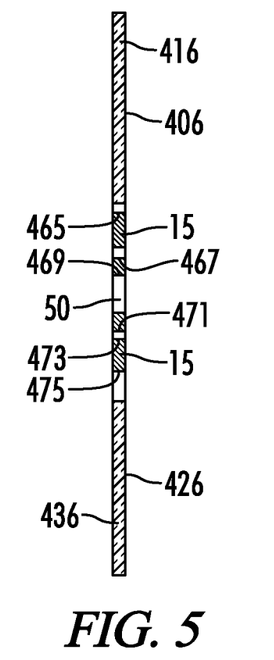
FIG. 5 depicts a cross-sectional view of a micro-fluidic reactor with in-plane micro-lenses in accordance with some embodiments of the present disclosure.

Note that section line 5 represents a perspective of a cross-sectional view of micro-fluidic reactor 10 as depicted by FIG. 5 and described in further detail below.

The substrate 15 of FIG. 4 may be configured to facilitate monitoring of reagent fluids in micro-channel 50 using signals from optical fibers (e.g., the plurality of source fibers 412, 414, and 416 and plurality of fibers detection fibers 432, 434, and 436). In order to achieve this, substrate 15 may be configured so that the optical fibers are aligned across micro-channel 50. In some embodiments, each of the first plurality of slots 402, 404, and 406 may be positioned such that a longitudinal axis of each of the first plurality of slots 402, 404, and 406, and the second plurality of slots 422, 424, and 426 is orthogonal to a longitudinal axis of the micro-channel 50. As depicted by FIG. 4, each of the first plurality of slots 402, 404, and 406 may be positioned such that it is approximately in alignment with a corresponding slot of the second plurality of slots 422, 424, and 426. For example, a longitudinal axis of slot 402 may be positioned such that it is approximately aligned with a longitudinal axis of slot 422. Similarly, slot 404 may be aligned with slot 424 such that each of slots 404 and 424 shares approximately the same longitudinal axis. Slot 406 may be aligned with slot 426 such that each of slots 406 and 426 shares approximately the same longitudinal axis. In this regard, when positioned in any of the first plurality of slots 402, 404 or 406, a source fiber 412, 414 or 416 may be aligned with a detection fiber 432, 434 or 436 positioned in a corresponding slot of the second plurality of slots 422, 424 or 426. Other configurations and quantities of slots and optical fibers may be present in substrate 15 in other embodiments.

As an example of enhancement of fiber-to-fiber optical power coupling using in-plane micro-lenses, FIG. 4 depicts placement of source fiber 412 and detection fiber 432 at a small distance from micro-channel 50, and placement of source fiber 414 and detection fiber 434 at an increased distance from micro-channel 50 relative to fiber 432. In the embodiment of FIG. 4, no micro-lenses are present between either of source fiber 412 and detection fiber 432 or source fiber 414 and detection fiber 434. It has been observed that fiber-to-fiber optical power coupling increases as a distance between source fiber and detection fiber decreases (e.g., due to spread of light over distance). Thus, where, as in the embodiment of FIG. 4, a distance between source fiber 414 and detection fiber 434 exceeds a distance between source fiber 412 and detection fiber 432, a measured optical power of a signal from source fiber 412 received by detection fiber 432 may exceed a measured optical power of a signal from source fiber 414 received by detection fiber 434. Nevertheless, any distance between a source and detection fiber may result in a loss of fiber-to-fiber optical power coupling performance (e.g., optical power).

In some embodiments, micro-lenses may improve fiber-to-fiber optical power coupling performance over a performance that is possible when a distance between a source fiber and detection fiber is reduced (e.g., in embodiments where source fiber 412 and detection fiber 432 may be substantially coterminous with one or more walls of micro-channel 50). As noted above, a power of an optical signal detected by detection fibers 432, 434 and 436 may be enhanced using in-plane micro-lenses, such as micro-lenses 465, 467, 469, 471, 473 and 475. In some embodiments, the first plurality of micro-lenses 465, 467 and 469 may be positioned between optical fiber 416 and micro-channel 50. Similarly, the second plurality of micro-lenses may be positioned between detection fiber 436 and micro-channel 50.

Note that a quantity and characteristics of each of the first plurality of micro-lenses 465, 467 and 469 and second plurality of micro-lenses 471, 473 and 475 may be selected to have a net effect on incident optical signals. In some embodiments, each of the first plurality of micro-lenses 465, 467 and 469 and second plurality of micro-lenses 471, 473 and 475 may have a shape for producing a desired effect on an optical signal (e.g., as described herein with regard to FIG. 2). In some embodiments, each of the first plurality of micro-lenses 465, 467 and 469 may refract light transmitted from source fiber 416 to form approximately collimated light following a focused path (e.g., path 225). Similarly, each of the second plurality of micro-lenses 471, 473, and 475 may refract light incident on the second plurality of micro-lenses 471, 473 and 475 to enhance an optical power of light received by detection fiber 436. A combination of the first plurality of micro-lenses 465, 467 and 469 and second plurality of micro-lenses 471, 473 and 475 may reduce optical spread by directing (e.g., focusing) a path of the optical signal from source fiber 416 to detection fiber 426. In this regard, fiber-to-fiber optical power coupling performance may be enhanced.

Note that each of the first plurality of micro-lenses 465, 467 and 469, and second plurality of micro-lenses 471, 473 and 475 may be produced by etching, as described above, or by other technique. Note also that substrate 15 may comprise any number of optical fibers, slots and micro-lenses having similar configurations to the configuration of source fiber 416, detection fiber 436, first plurality of micro-lenses 465, 467 and 469, and second plurality of micro-lenses 471, 473 and 475 in FIG. 4. In some embodiments, each source fiber and detection fiber pair (e.g., source fiber 416 and detection fiber 436) may comprise corresponding micro-lenses (e.g., first plurality 465, 467 and 469 and second plurality 471, 473 and 475) for achieving the functionality described herein.

FIG. 5 depicts a cross-sectional view of a micro-fluidic reactor with in-plane micro-lenses in accordance with some embodiments of the present disclosure. The various elements of the micro-fluidic reactor of FIG. 5 generally correspond to elements of the micro-fluidic reactor of FIG. 4 having corresponding reference numbers. The cross-sectional view of FIG. 5 illustrates the in-plane nature of the micro-lenses 465, 467, 469, 471, 473 and 475. A portion of each of source fiber 416 and detection fiber 436 is depicted. Optical signals provided from source fiber 416 may follow the path described above with regard to FIG. 4 and be detected by detection fiber 436. Each of micro-lenses 465, 467, 469, 471, 473 and 475 is depicted as having surfaces that are substantially parallel to walls of micro-channel 50, but in some embodiments, micro-lens surfaces may have various profiles for achieving a desired functionality. Note also that spacing between each of the elements of FIG. 5 may be altered as desired in some embodiments to achieve a desired functionality, such as for reaching a desired optical fiber-to-fiber coupling power.

Figure 6:
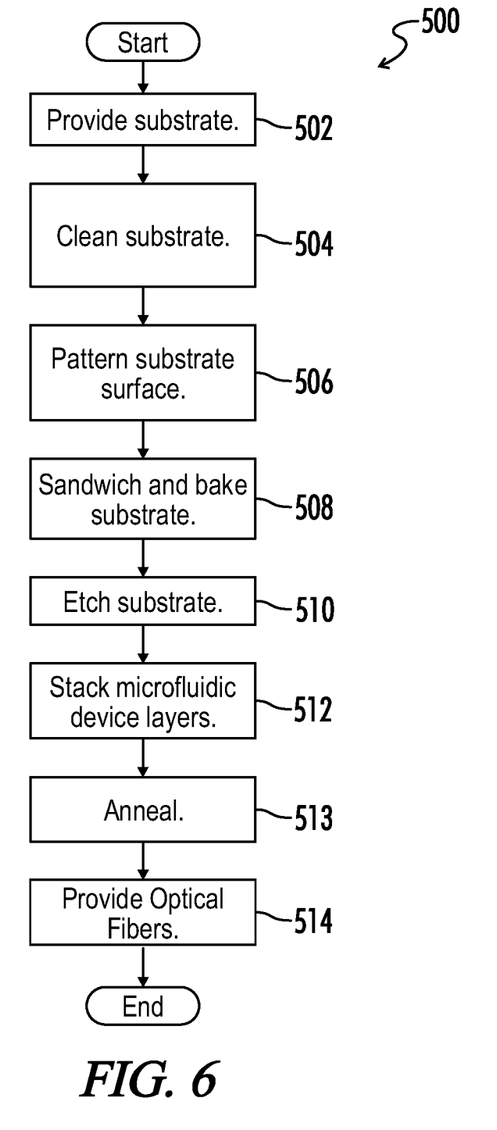
FIG. 6 depicts a flow chart illustrating exemplary methods for fabricating in-plane micro-lenses in accordance with some embodiments of the present disclosure.

FIG. 6 depicts a flow chart illustrating an exemplary method 500 for coating a glass substrate of a micro-fluidic reactor with a short-chain silane monolayer. Although particular techniques may be described for performing steps of the method 500, it will be understood that various other techniques may be possible in other embodiments, and that such techniques, although apparent to one of ordinary skill in the art are not discussed herein for sake of efficiency. At step 502, a substrate is provided, such as substrate 15. In some embodiments, the substrate 15 may be a photosensitive glass substrate, such as a photosensitive borosilicate glass (e.g., APEX glass) or otherwise, and may have appropriate properties for achieving the functionality of substrate 15 described herein (e.g., transparency, low auto-fluorescence, chemical resistance, thermal and electrical properties, compatibility with silanol based chemistries, etc.). Processing may continue to step 504 after a substrate 15 has been provided at step 502.

The substrate 15 may be cleaned at step 504, such as by rubbing with ethanol and a shed resistant cloth, or using other suitable material. The substrate 15 may be rinsed with ethanol, acetone and then with ethanol in sequence, followed by drying under a nitrogen stream. Other techniques for cleaning the substrate 15 may be possible in other embodiments. Once cleaning has been performed, processing may continue to step 506.

At step 506, one or more surfaces of the substrate 15 may be patterned prior to baking. In some embodiments, a desired pattern may be applied to the one or more surfaces of the substrate 15 using a photomask, such as a quartz photomask or otherwise. In an embodiment, a quartz photomask is applied to a surface of the substrate 15. The quartz photomask may have a shape, contours or area that corresponds to a desired shape or area of features of the substrate 15, such as one or more micro-channels 50, a reaction chamber 52, one or more reagent ports 55, one or more slots (e.g., the first plurality of slots 402, 404, and 406 and the second plurality of slots 422, 424, and 426), a plurality of micro-lenses (e.g., first plurality of micro-lenses 465 467, and 469 and second plurality of micro-lenses 471, 473 and 475) or other feature. After the quartz photomask is applied to the substrate 15, a dose of light may be applied (e.g., UV light) for transferring a pattern from the photomask to the substrate 15. After the substrate 15 has been patterned, processing may continue to step 508.

At step 508, the substrate 15 may be sandwiched between two adjacent substrates and baked to reveal the pattern transferred through UV illumination. The adjacent substrates may comprise any suitable material, but in an exemplary embodiment, each of the two adjacent substrates comprises alumina. Baking may occur after placement of the adjacent substrates. In some embodiments, the baking may comprise a two-step baking process. For example, a temperature of the substrate 15 and adjacent substrates may be ramped up from room temperature to approximately 500° C. at a rate of approximately 6° C./min., held constant for approximately 75 minutes, then ramped up again to approximately 555° C. at 2° approximately C/min. The temperature may then be allowed to dwell (e.g., stabilize) for approximately 80 minutes at 555° C., before the temperature is ramped down at approximately 2° C./min. to room temperature. After the substrate 15 and adjacent substrates reach room temperature, processing may continue to step 510.

At step 510, the substrate 15 may undergo etching. In some embodiments, etching may be performed using any suitable etching component, but in an exemplary embodiment, the substrate 15 may be exposed to (e.g., dipped, immersed, or otherwise) hydrofluoric acid (HF) to perform etching. In some embodiments, the substrate 15 may be immersed in approximately 10% HF for approximately 1 hour or other time. In an embodiment, etching of patterned areas of the substrate 15 may occur during exposure of the substrate 15 to HF. A thickness of other areas of the substrate 15 may be altered (e.g., reduced), although complete etching or reduction of material may not occur. As a result of the etching process, a boundary between a portion of a surface of substrate 15 exposed to UV light and a portion not exposed to UV light may define a boundary of a feature of substrate 15 (e.g., a wall of micro-channel 50 or other feature). Thus, a plurality of such boundaries may define each feature present in the substrate 15. After etching of the substrate 15 is complete, processing may continue to step 512.

At step 512, any additional layers of micro-fluidic device 10 may be added to substrate 15. For example, in some embodiments, a micro-fluidic device may comprise a reservoir, drain, or other layers not specifically shown in FIG. 1 or FIG. 4. In some embodiments, such additional layers may be stacked in a desired configuration along with substrate 15 as part of a process for fabricating micro-fluidic reactor 10. In some embodiments, one or more of the additional layers may comprise a glass layer. In this regard, one or more additional layers that will be adjacent to substrate 15 in a final configuration of micro-fluidic reactor 10 may be stacked or positioned adjacent to substrate 15. After any additional layers of micro-fluidic device 10 have been positioned adjacent to substrate 15 as desired, processing may continue to step 513.

At step 513, the substrate 15 may undergo thermal annealing for sealing various substrates (e.g., glass substrate 15 and adjacent substrates described above) of the micro-fluidic reactor 10 and reducing surface roughness of the micro-channels 50 of substrate 15 caused by baking and etching. In some embodiments, exposure of the substrate 15 to increased temperatures during baking (e.g., at step 508) and to HF during the etching process (e.g., at step 510) may produce inconsistencies or variations on one or more surfaces of the substrate 15. Such inconsistencies or variations may result in a surface roughness that exceeds a desired amount of surface roughness. In some embodiments, it may be desirable to reduce surface roughness within a micro-channel 50 as much as possible (e.g., for facilitating improved EOF or otherwise). In an exemplary embodiment, a roughness of surfaces of the substrate 15 may be reduced by thermal annealing. As a result of annealing, surface tension forces may bond multiple substrates (e.g., glass, alumina, or other substrate) together near transition temperatures for a material of the respective substrate of the micro-fluidic reactor 10. Near a transition temperature for glass, multiple glass layers (e.g., variations and inconsistencies of glass surfaces) may be bound together to bond the multiple layers and smooth roughened surfaces. The annealing may include ramping a temperature to approximately 535° C. from room temperature at approximately 6° C./min., an approximately 7 hour dwell, then ramping down to room temperature at approximately 2° C./min. Other annealing techniques may be used in other embodiments. After the substrate 15 has reached room temperature, processing may continue to step 514.

At step 514, one or more optical fibers may be inserted into the slots of the glass substrate 15 created as part of the etching process at step 510. The one or more optical fibers may be positioned within the slots as desired for achieving fiber-to-fiber optical power coupling as described herein. In some embodiments, one or more optical fibers (e.g., source fibers 412, 414, or 416) coupled to a light source (e.g., light source 20) may be inserted into one or more slots (e.g., slots 402, 404, or 406), and one or more optical fibers (e.g., detection fibers 432, 434 or 436) coupled to a light detector (e.g., light detector 30) may be inserted into one or more slots (e.g., 422, 424, or 426). Optical fibers may be provided to other features of substrate 15 in other embodiments. In some embodiments, one or more optical fibers may be provided prior to the annealing step 513, such as when the one or more optical fibers comprise a glass material. After all optical fibers have been provided, processing may end.

Now, therefore, the following is claimed:

1. A micro-fluidic reactor, comprising:
a substrate having a micro-channel, a reaction chamber, a first lens, and a second lens;
a first optical fiber for receiving light from a light source, the first optical fiber passing through the substrate; and
a second optical fiber for receiving the light from the first optical fiber, the second optical fiber passing through the substrate,
wherein the first optical fiber and the second optical fiber are positioned on opposite sides of the micro-channel or the reaction chamber such that the light passes from the first optical fiber through the micro-channel or the reaction chamber to the second optical fiber, wherein the first lens and the second lens are positioned within a path of the light from the first optical fiber to the second optical fiber, wherein the first lens is between (1) the first optical fiber and (2) the micro-channel or the reaction chamber, wherein the second lens is between (a) the second optical fiber and (b) the micro-channel or the reaction chamber, wherein the first lens is positioned to focus the light on the second lens, and wherein the second lens is positioned to focus the light on the second optical fiber.

2. The micro-fluidic reactor of claim 1, wherein the first lens is configured to focus the light on the second lens such that the light when passing from the first lens through the micro-channel or the reaction chamber to the second lens is collimated.

3. The micro-fluidic reactor of claim 2, wherein the first lens is positioned on a first wall of the micro-channel or the reaction chamber, and wherein the second lens is positioned on a second wall of the micro-channel or the reaction chamber.

4. The micro-fluidic reactor of claim 1, wherein the first lens is a toric lens.

5. The micro-fluidic reactor of claim 4, wherein the second lens is a toric lens.

* * * * *